US009625370B2

(12) United States Patent
Bawolek

(10) Patent No.: US 9,625,370 B2
(45) Date of Patent: Apr. 18, 2017

(54) MICROSCOPE WITH SPECTROSCOPIC CAPABILITY

(71) Applicant: Empire Technology Development LLC, Wilmington, DE (US)

(72) Inventor: Edward J. Bawolek, Chandler, AZ (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 95 days.

(21) Appl. No.: 14/417,135

(22) PCT Filed: Aug. 26, 2014

(86) PCT No.: PCT/US2014/052588
§ 371 (c)(1),
(2) Date: Jan. 23, 2015

(87) PCT Pub. No.: WO2016/032431
PCT Pub. Date: Mar. 3, 2016

(65) Prior Publication Data
US 2016/0061717 A1    Mar. 3, 2016

(51) Int. Cl.
*G01J 3/46* (2006.01)
*G01N 21/25* (2006.01)
(Continued)

(52) U.S. Cl.
CPC .......... *G01N 21/255* (2013.01); *G01J 3/0264* (2013.01); *G01J 3/10* (2013.01);
(Continued)

(58) Field of Classification Search
CPC .......... G01N 21/255; G01N 2201/062; G01N 2201/0612; G01J 3/10; G01J 3/28; G02B 21/06
(Continued)

(56) References Cited

U.S. PATENT DOCUMENTS 6,055,095 A    4/2000 Bawolek
6,211,521 B1    4/2001 Bawolek et al.
(Continued)

OTHER PUBLICATIONS

"Nature's Color Identifier™ The ChromaID™ Story," accessed at https://web.archive.org/web/20131213193536/http://www.visualant.net/resources/Visualant_The_ChromaID_Story.pdf, accessed on Jan. 19, 2015, pp. 1-10.
(Continued)

*Primary Examiner* — Abdullahi Nur
(74) *Attorney, Agent, or Firm* — Turk IP Law, LLC

(57) ABSTRACT

Technologies are generally described for determination of a spectral profile of a sample. A microscope with spectroscopic capability may include a multitude of light sources, one or more photo detectors, and an analysis module. The microscope may be a table-top microscope or a hand-held microscope. The light sources may be configured to illuminate at least one portion of the sample, the photo detectors may be configured to detect returned light from the sample in response to the illumination, and the analysis module may be configured to analyze the detected light to determine a spectral profile of the sample. In some examples, the spectral profile of the sample may be compared to a spectral profile of a reference sample to evaluate the sample, where the sample may be evaluated to determine an identity, a quality, an authenticity, a composition, a density, a reflectivity, and/or an amount of the sample.

20 Claims, 9 Drawing Sheets

(51) Int. Cl.
*G01J 3/10* (2006.01)
*G01J 3/28* (2006.01)
*G02B 21/06* (2006.01)
*G02B 21/08* (2006.01)
*G02B 21/16* (2006.01)
*G01J 3/02* (2006.01)
*G01J 3/50* (2006.01)

(52) U.S. Cl.
CPC ............... *G01J 3/28* (2013.01); *G01J 3/2803* (2013.01); *G01J 3/50* (2013.01); *G02B 21/06* (2013.01); *G02B 21/084* (2013.01); *G02B 21/088* (2013.01); *G02B 21/16* (2013.01); *G01J 2003/102* (2013.01); *G01N 2201/0221* (2013.01)

(58) Field of Classification Search
USPC .................................................. 356/402–425
See application file for complete search history.

(56) References Cited

U.S. PATENT DOCUMENTS

| | | |
|---|---|---|
| 7,102,817 B1 | 9/2006 | Wu |
| 7,330,257 B2 | 2/2008 | Kuroiwa et al. |
| 7,586,674 B2 | 9/2009 | O'connell |
| 8,076,630 B2 | 12/2011 | Schowengerdt et al. |
| 8,358,851 B2 | 1/2013 | Wu |
| 8,368,878 B2* | 2/2013 | Furness, III ............. G01J 3/02 356/445 |
| 2012/0140056 A1* | 6/2012 | Pribenszky .......... G02B 21/361 348/79 |
| 2012/0307081 A1 | 12/2012 | Dewald |

OTHER PUBLICATIONS

"Spectral Imaging Microscopy Literature References," accessed at https://web.archive.org/web/20140716115230/http://www.microscopyu.com/references/spectralimaging.html, accessed on Jan. 19, 2015, pp. 1-4.

"StellarSCOPE™ System for Microscopy," accessed at http://stellarnet.us/PopularConfiguration_microscopy.htm, accessed on Jan. 19, 2015, pp. 1-4.

"Visualant's ChromaID™ Technology," accessed at https://web.archive.org/web/20131209233826/http://visualant.net/resources/Visualant_ChromaID_Technical_White_Paper.pdf, accessed on Jan. 19, 2015, pp. 1-3.

Garini, Y., et al., "Spectral imaging: Principles and applications," Journal of International Society for Advancement of Cytometry, vol. 69A, No. 8, pp. 735-747 (Aug. 1, 2006).

International Search Report and Written Opinion for counterpart International Patent Application No. PCT/US2014/052588 mailed Dec. 9, 2014.

* cited by examiner

MICROSCOPE WITH SPECTROSCOPIC CAPABILITY

CROSS-REFERENCE TO RELATED APPLICATION

This Application is the U.S. National Stage filing under 35 U.S.C §371 of PCT Application Ser. No. PCT/US14/52588 filed on Aug. 26, 2014. The PCT Application is herein incorporated by reference in its entirety.

BACKGROUND

Unless otherwise indicated herein, the materials described in this section are not prior art to the claims in this application and are not admitted to be prior art by inclusion in this section.

In a variety of scientific, industrial, financial, and legal activities, spectroscopic information may need to be acquired from a small and/or microscopic sample area to evaluate a substance, product, and/or document. For example, an authenticity of a driver's license may need to be verified based on a spectral profile determined from a small portion of the license. Therefore, integrated microscope and image sensor units may find increasing application in such activities where microscopic evaluations may be needed. However, current costs to produce and implement such units are extremely high, and greater portability is needed.

Accordingly, methods and/or apparatuses to determine a spectral profile of a sample could use improvements and alternative or additional solutions in order to provide a cost-effective method to allow microscopic portions of a sample to be evaluated based on a determined spectral profile.

SUMMARY

The present disclosure generally describes techniques to determine a spectral profile of a sample employing a microscope.

According to some examples, microscopes with spectroscopic capability may be described. An example microscope may include a plurality of light sources positioned within the microscope, where the light sources may be configured to illuminate at least one portion of a sample; and one or more photo detectors positioned within the microscope such that the light sources surround the photo detectors, where the photo detectors may be configured to detect returned light from the portion of the sample in response to the illumination. The example microscope may also include an analysis module configured to analyze the detected light to determine a spectral profile of the portion of the sample.

According to other examples, systems to determine a spectral profile of a sample are described. An example system may include an imaging sub-system and an analytics sub-system. The imaging sub-system may include an illumination module configured to illuminate at least one portion of the sample with light from a plurality of light sources positioned within a microscope; and a detection module configured to detect returned light from the portion of the sample in response to the illumination at one or more photo detectors positioned within the microscope. The analytics sub-system may include one or more servers coupled to the imaging sub-system, the one or more servers configured to execute a profiling module configured to analyze the detected light to determine a spectral profile of the portion of the sample; and an evaluation module configured to evaluate one or more characteristics of the at least one portion of the sample based on the determined spectral profile.

According to further examples, methods to determine a spectral profile of a sample are provided. An example method may include sequentially illuminating at least one portion of the sample at a variety of wavelengths from a plurality of light sources positioned in a microscope, detecting returned light from the portion of the sample in response to the illumination at one or more photo detectors positioned in the microscope, and analyzing the returned light to determine the spectral profile of the portion of the sample.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1A:
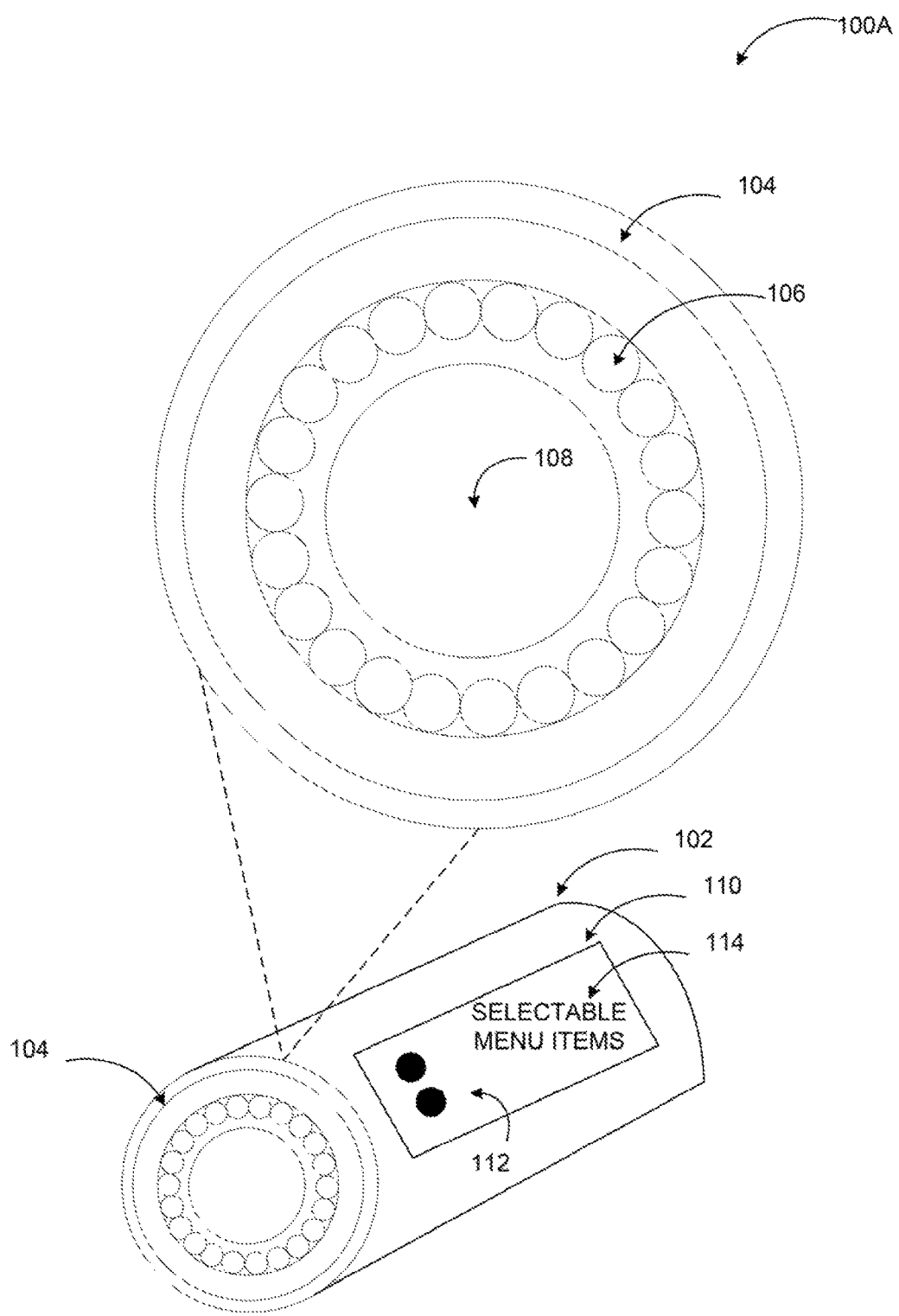
FIGS. 1A, 1B, and 1C illustrate example configurations of a microscope configured to illuminate a sample and detect returned light from the sample in response to the illumination.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, among other things, to methods, apparatus, systems, devices, and/or computer program products related to determination of a spectral profile of a sample employing a microscope.

Briefly stated, technologies are generally described for determination of a spectral profile of a sample. A microscope with spectroscopic capability may include a multitude of light sources, one or more photo detectors, and an analysis module. The microscope may be a table-top microscope or a hand-held microscope, for example. The light sources may be configured to illuminate at least one portion of the sample, the photo detectors may be configured to detect returned light from the sample in response to the illumination, and the analysis module may be configured to analyze the detected light to determine a spectral profile of the sample. In some examples, the spectral profile of the sample may be compared to a spectral profile of a reference sample to evaluate the sample, where the sample may be evaluated to determine an identity, a composition, a quality, an authenticity, a density, a reflectivity, and/or an amount of the sample.

Figure 1B:
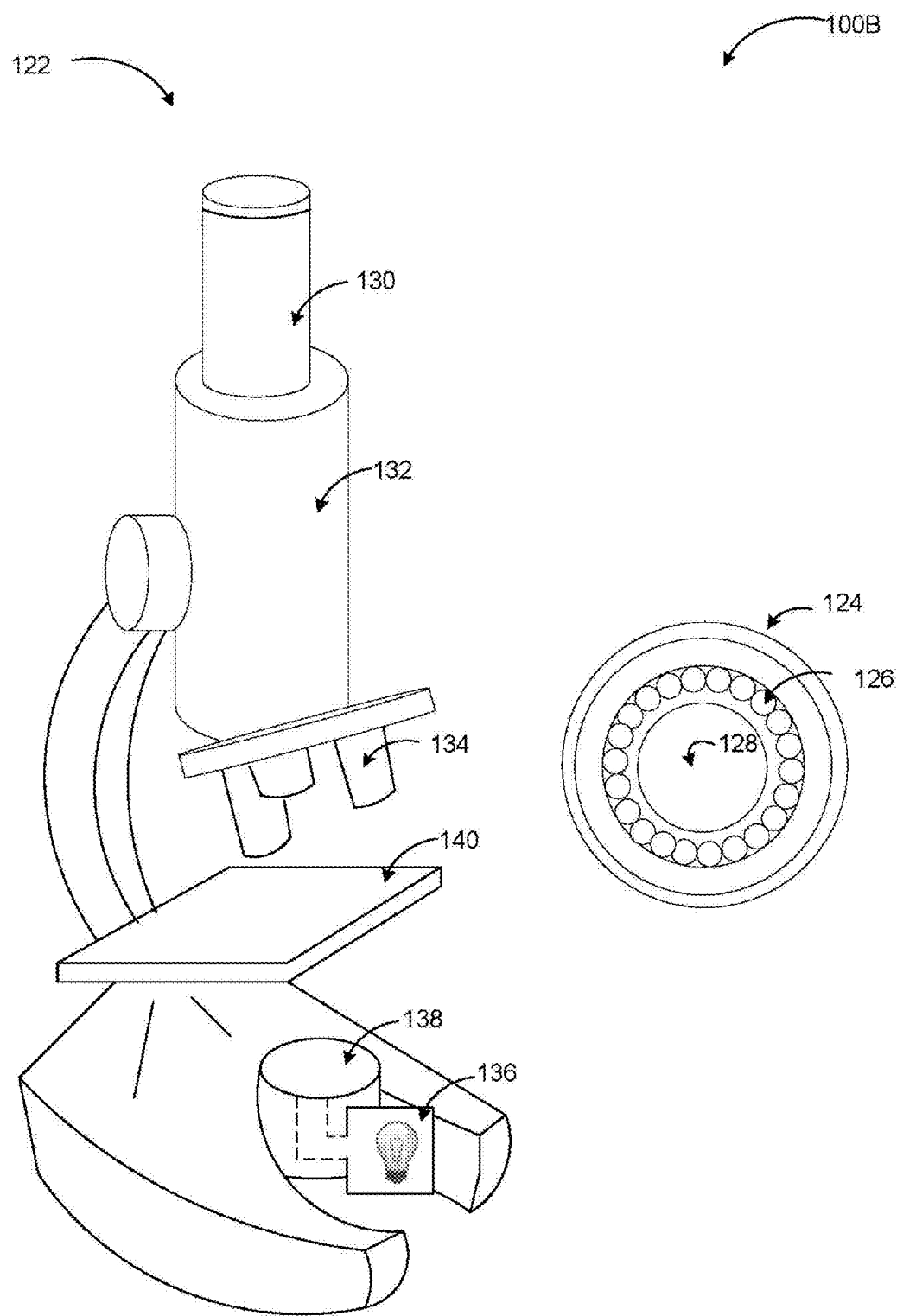
Figure 1C:
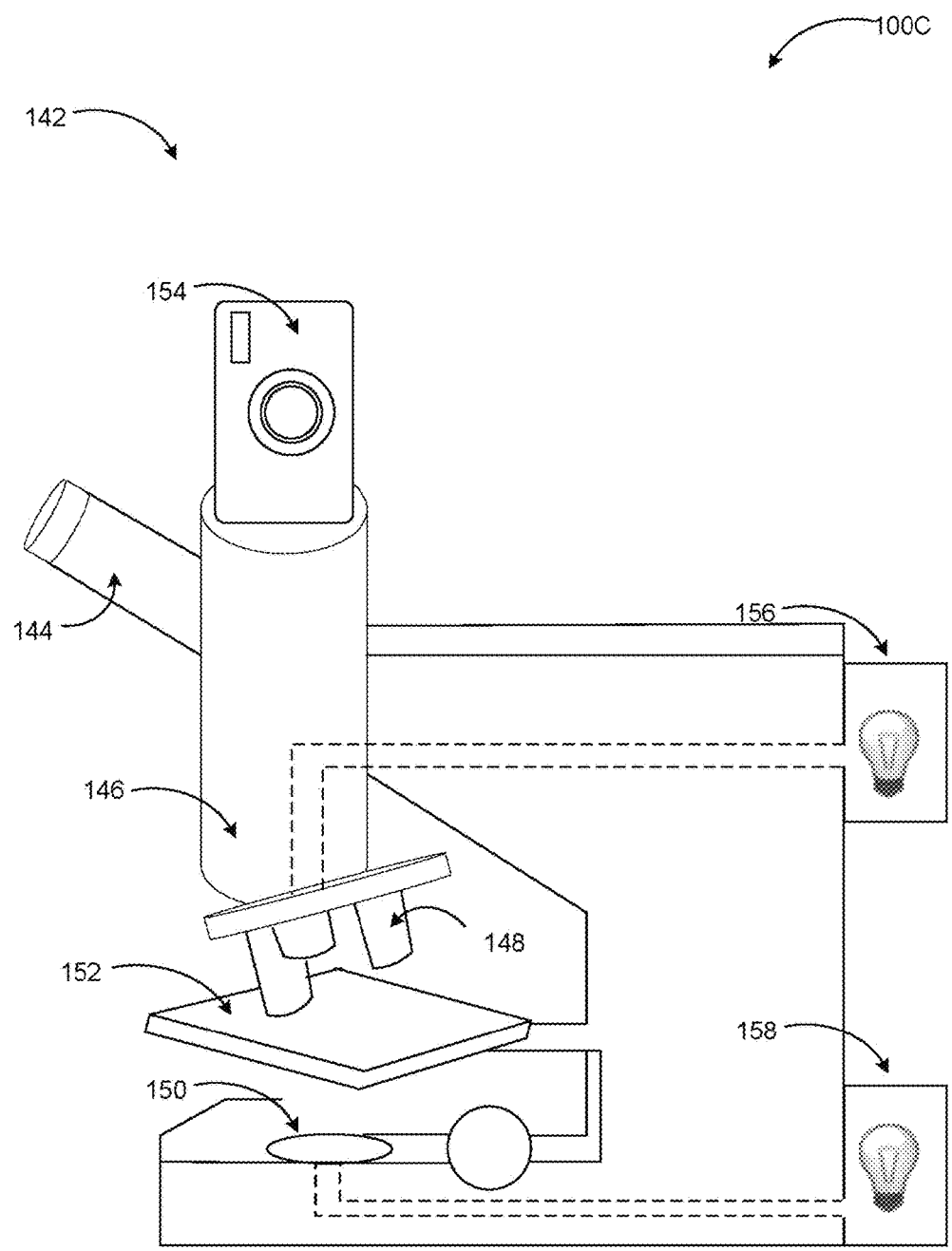

FIGS. 1A, 1B, and 1C illustrate example configurations of a microscope configured to illuminate a sample and detect returned light from the sample in response to the illumination, arranged in accordance with at least some embodiments described herein.

As shown in FIG. 1A, diagram 100A, an example microscope 102 may be a hand-held microscope. The microscope 102 may include one or more optical elements, such as a lens 104, a multitude of light sources 106, and one or more photo detectors 108 positioned within the microscope 102. The lens may have a selectable and/or adjustable magnification range from approximately about 10× or 20× to approximately about 250×, with some lenses being adjustable up to a magnification of 500×. The magnification selected may be a function of a degree of detail needed and a size of a sample being characterized and/or evaluated. Other optical elements within the microscope 102 may include reflectors partial reflectors, and/or may be used as magnifying optics for the one or more photo detectors 108, for example. In some embodiments, one or more polarizer elements may be integrated with the light sources 106 and the photo detectors 108 to provide a polarized light microscope. The polarized light microscope may be configured to provide a glare control, a discrimination of roughness variations, and a relative stress indication, for example.

The microscope 102 may also include an analysis module. The analysis module may be integrated with the microscope 102 and/or may be a part of a computing device coupled to the microscope 102 through wired or wireless communication means. For example, the microscope 102 may be coupled to the computing device through a Universal Serial Bus (USB) cable. Alternately, the microscope 102 may be coupled to the computing device via WIFI, Bluetooth, and/or Near-Field Communication (NFC), which may provide further portability for the microscope 102. One or more controls may be incorporated into the microscope 102, including a focusing and/or magnification knob, and a button element which may trigger an image capture by the microscope 102 causing automatic transmission via the USB cable, WIFI, Bluetooth, and/or Near-Field Communication (NFC) to the computing device. In other examples, the analysis module may be solely integrated with the microscope 102 causing image and/or spectral data obtained by the microscope 102 to be stored in memory local to the microscope 102 for subsequent download and/or comparison with a database. For example, the image and/or spectral data may be stored in a micro-Secure Digital (SD) card of the microscope 102.

The light sources 106 may include light emitting diodes (LEDs), laser diodes, white light sources, UV light sources, infrared light sources, red light sources, orange light sources, yellow light sources, green light sources, blue light sources, and/or violet light sources. The light sources 106 may be selected based on a color and/or identity of a sample to be illuminated. In some embodiments, a category of the sample and/or physical description thereof may be input by a user. For example, the user may enter "white, crystalline substance" into the microscope 102 using buttons 112, selectable menu items 114, voice recognition, and/or or other suitable user input 110. The light sources 106 may be configured to illuminate at least one portion of the sample with light, where the lens 104 may converge incident light from the light sources 106 on and around the portion of the sample to illuminate the portion of the sample. In some examples, the light sources 106 may include one or more focusing optics to help direct the light toward a central region under the microscope 102 where the portion of the sample is positioned, and/or to collimate the light from an emitter, such as an LED, which can otherwise lack directionality. In some embodiments, an indicator light source, such as light from white LED light sources may be used initially to illuminate the sample to inspect and determine a target area on the sample for evaluation.

In some examples, the portion of the sample may be illuminated with the light at a variety of wavelengths in a sequential order or in a random order. One or more of the light sources 106 may be operable to emit the light at wavelengths in part or in all of an optical portion of the electromagnetic spectrum, including the visible portion, near-infrared portion and/or near ultraviolet portions of the electromagnetic spectrum. Additionally, or alternatively, the light sources 106 may be operable to emit light at wavelengths in other portions of the electromagnetic spectrum, such as the infrared, ultraviolet, and/or microwave portions.

In some embodiments, at least one of the light sources 106 may be operable to emit the light in or at a different wavelength the other light sources. For example, one or more of the light sources 106 may emit the light at a wavelength around 450 nm, one or more light sources 106 may emit the light at a wavelength around 500 nm, and at least one of the light sources 106 may emit the light at a wavelength around 550 nm. In some embodiments, each of the light sources 106 may emit light at a different wavelength. Using light sources that emit light at different wavelengths may maximize a number of distinct samples that may be captured from a fixed number of light sources. This may be of particular use when the microscope is smaller, such as the hand-held microscope 102, and/or has limited space or footprint for the light sources 106.

The distribution of spectral content for each of the light sources 106 may vary as a function of drive level (for example, current, voltage, and duty cycle), temperature, and/or other environmental factors, depending on a type of the light sources 106. Such variation may be actively employed to operate one or more of the physical light sources as a plurality of "logical light sources", where each of the logical light sources may be operable to provide a respective emission spectrum from a respective physical source. For example, a peak wavelength at which each of the light sources 106 emits light may be varied by altering and/or adjusting a drive level and/or a temperature. Adjustment of the drive level and/or temperature may cause the peak wavelength to shift, allowing each of the light sources 106 to emit light at a different wavelength such that the portion of the sample may be illuminated with light at a variety of different wavelengths.

The photo detectors 108 may include photodiodes, photomultiplier tubes, CMOS image sensors, CCDs, infrared sensors, thermal sensors, and/or micro-channel plates. The photo detectors 108 may be positioned within the microscope such that the light sources 106 surround the photo detectors 108, where the light sources may be positioned in a circular arrangement, an elliptical arrangement, a rectangular arrangement, or a triangular arrangement. In some examples, each of the photo detectors 108 may include a lens configured to create a focused image of a surface of the portion of the sample. The photo detectors 108 may be configured to detect returned (that is multiple reflected, transmitted, and/or scattered) light from the portion of the sample in response to the illumination through separate red, green, and blue color channels. In some embodiments, the returned light may be detected at the photo detectors through an additional color channel to provide spectral discrimination. In other embodiments, the microscope 102 may include at least one light blocking filter, where the filter may be configured to reduce a portion of light from the light sources 106 directed to the photo detectors 108 when illuminating the portion of the sample.

The analysis module of the microscope 102 may be configured to analyze the detected light to determine a spectral profile of the portion of the sample. For example, the analysis module may record a response from the photo detectors 110 as a function of the light sources 106 selected and the sources' intensity (i.e., a power and/or current supplied to the light sources 106). The response may be compared to tabulated values in a database. In a comprehensive spectral analysis, the response and comparison process may be repeated for a plurality of the light sources 106 to build a detailed collection of data comprising multiple wavelengths of light.

In some embodiments, the analysis module may be further configured to evaluate the portion of the sample by comparing the spectral profile of the portion of the sample to a spectral profile of a reference sample. Furthermore, if the category of the sample and/or physical description thereof was input by the user, the analysis module may then compare the spectral profile of the portion of the sample with a restricted selection of spectral profiles of reference samples, based on the selected category. The sample may be evaluated to determine an identity, a composition, a quality, an authenticity, a density, a reflectivity, and/or an amount of the sample. For example, an identity of an unknown substance may be determined, a purity of a product may be evaluated for quality control, and an authenticity of a financial, legal, and/or medical document may be verified, among other examples.

In some embodiments, the photo detectors 108 may be configured to capture an image in addition to detecting the reflected, transmitted, and/or scattered light. The spectral profile determined from analysis of the detected light and the image data may be linked together automatically for improved analysis. Successful analysis may be indicated to a user of the microscope 102. Alternately, further data collection may be requested by the user or automatically obtained in response to an unsuccessful analysis.

The microscope 102 being hand-held and compact may provide a portability that extends the functionality of the microscope 102. In an example scenario, a law enforcement officer may be able to employ the microscope 102 on-site to identity an unknown white substance found in a car during a routine stop for a traffic violation. If the substance is identified as an illegal substance, the officer may take immediate action prior to the perpetrator being released. Furthermore, the microscope 102 may be incorporated with other portable devices, such as a flashlight, a pen, a Radio-Frequency Identification (RFID) reader, a smart phone and/or a head-mounted display, among other examples, to allow a user to quickly determine a spectral profile of a sample anywhere, anytime. In the above scenario, the microscope 102 may be incorporated with a flashlight for a convenience of the law enforcement officer, for example.

In further examples, the image of the portion of the sample captured by the photo detectors may be transmitted to a portable electronic device, such as the smart phone or head-mounted display, and displayed on the display thereof. The spatial location and extent of the portion may be adjusted using, for example, the magnifying optics within the microscope. In some examples, an application on the portable electronic device may be used to control the microscope. For example, once a desired portion of the sample is selected, a button icon displayed on the screen of the portable electronic device may be touched, initiating collection of spectral data to determine the spectral profile. The spectral data may be displayed and/or stored in memory (e.g. of the portable electronic device) together with the image of the portion of the sample from which it was collected.

As shown in FIG. 1B, diagram 100B, an example microscope 122 may be a table-top microscope. The microscope 122 may include an eyepiece 130 comprising at least one lens, a body tube 132 connecting the eyepiece to one or more objectives 134 each comprising a lens, an illumination source 136, a diaphragm 138 configured to vary the intensity and size of light projected upward from the illumination source 136, and a stage 140. The lenses may have a magnification selectable or adjustable between magnifications of 5×, 10×, 20×, 50×, 100×, 250×, for example, where the magnification selected may be a function of a degree of detail needed and a size of a sample being characterized and/or evaluated. For example, conductive traces on a modern printed circuit board may be as narrow in width as 50 micro-meters. To image and characterize a gold plating on these traces, a relatively higher magnification of 100× to 250× may be employed so that a relative portion of the captured image occupied by the sample is at least 50%. In another example, if a color of a button-sized (5 mm diameter) paint chip from an historic building restoration is being characterized, a lower magnification of approximately 10× to 20× may be sufficient. The microscope may further include a multitude of light sources 126 and one or more photo detectors 128. The light sources 126 and photo detectors 128 may be positioned internally within the body tube 132, positioned internally within the objectives 134, and/or positioned internally within the illumination source 136. The microscope 122 may further include an analysis module. The analysis module may be integrated with the microscope 122 and/or may be a part of a computing device coupled to the microscope 122 through wired or wireless communication means.

The light sources 126 may include light emitting diodes (LEDs), laser diodes, white light sources, UV light sources, infrared light sources, red light sources, orange light sources, yellow light sources, green light sources, blue light sources, and/or violet light sources. The light sources 126 may be configured to illuminate at least one portion of a sample positioned on the stage 140 with light, where a lens, which may be the lens associated with the eyepiece 130 or one or more of the lenses associated with the objectives 134, may converge incident light from the light sources 126 on and around the portion of the sample to illuminate the portion of the sample. In some embodiments, the portion of the sample may be illuminated with the light at a variety of wavelengths in a sequential order or in a random order. In other embodiments, light from white, LED light sources may be used to illuminate the sample to initially inspect and determine a target area on the sample for evaluation.

The photo detectors 128 may include photodiodes, photomultiplier tubes, CMOS image sensors, CCDs, infrared sensors, thermal sensors, and/or micro-channel plates. The photo detectors 128 may be positioned within the microscope such that the light sources 126 surround the photo detectors 128, where the light sources may be positioned in a circular arrangement, an elliptical arrangement, a rectangular arrangement, or a triangular arrangement. In some examples, the light sources may be positioned in array. Alternately, the photo detectors 128 may be positioned so as to be physically separate from the light sources 126. The photo detectors 128 may be configured to detect reflected, transmitted, and/or scattered light from the portion of the sample in response to the illumination through separate red, green, and blue color channels. In some embodiments, the reflected, transmitted, and/or scattered light may be detected at the photo detectors through an additional color channel to provide spectral discrimination.

The analysis module of the microscope 122 may be configured to analyze the detected light to determine a spectral profile of the portion of the sample. In some embodiments, the analysis module may be further configured to evaluate the portion of the sample by comparing the spectral profile of the portion of the sample to a spectral profile of a reference sample. The sample may be evaluated to determine an identity, a composition, a quality, an authenticity, a density, a reflectivity, and/or an amount of the sample. For example, an identity of an unknown substance may be determined, a purity of a product may be evaluated for quality control, and an authenticity of a financial, legal, and/or medical document may be verified, among other examples.

The microscope 122, being a table-top device, may not offer the portability discussed in conjunction with microscope 102 of FIG. 1A. However, the microscope 122 may be useful in industrial and/or scientific settings. For example, an organic chemist may want to evaluate a purity of a recrystallized substance. The chemist may employ the table-top microscope, which may be positioned on a work bench of a laboratory, to determine a spectral profile of the substance and evaluate the purity of the substance based on the spectral profile. Furthermore, the microscope 122 may be configured such that a variety of different illumination and detection modules may be interchanged within the microscope 122, so as to customize response to a wide variety of materials. For example, the microscope 122 may include a color camera to characterize color samples such as paint chips. Alternately, the microscope 122 may be configured with an infrared-sensitive camera module to characterize biological samples or polymers.

As shown in FIG. 1C, diagram 100C, another configuration of a table-top microscope 142 may include additional components, such as a camera 154, an episcopic illuminator 156, and/or a diascopic illuminator 158, for example. Similar to the table-top microscope discussed in conjunction with FIG. 1B, the microscope 142 may include an eyepiece 144 comprising at least one lens, a body tube 146 connecting the eyepiece 144 to one or more objectives 148 each comprising a lens, one or more illumination sources (i.e., the episcopic illuminator 156 and/or the diascopic illuminator 158), a diaphragm 150 configured to vary the intensity and size of light projected from the diascopic illuminator 158, and a stage 152. As previously discussed, the lenses may have a magnification selectable or adjustable between magnifications of 5×, 10×, 20×, 50×, 100×, 250×, for example.

The camera 154 may be an image sensor, such as a CCD or CMOS image sensor, for example. The camera 154 may be positioned superior to the body tube 146 using a mount adapter, for example. The camera 154 may be configured to capture images of the portion of the sample, and the image data may be linked together automatically with spectral analysis data for the portion of the sample to enhance the analysis and/or evaluation. In some examples, the camera 154 may be interchanged within the microscope 142, dependent on the sample, so as to customize response to a wide variety of materials. For example, the camera 154 mounted may be a color camera if a color of a sample is to be characterized. For further example, the camera 154 mounted may be an infrared-sensitive camera module if biological samples or polymers are to be characterized.

As previously discussed, the illuminators may include the episcopic illuminator 156 and/or the diascopic illuminator 158. The episcopic illuminator 156 may be configured to illuminate the portion of the sample with light from above the sample employing reflected illumination. A variety of orientations of light may be used, ranging from on-axis to oblique to optimize sample features and characteristics of interest, for example. In some embodiments, the episcopic illuminator 156 may be a tungsten illuminator, a ring light mounted on a body of at least one of the objectives 148, and a coaxial illuminator. The diascopic illuminator 158 may be configured to illuminate the portion of the sample with light from underneath the sample employing transmitted illumination. The transmitted illumination may be brightfield, polarized, oblique, or darkfield illumination, for example. In some embodiments, the light transmitted by the diascopic illuminator 158 may be at an oblique angle to provide a greater contrast and to produce images of enhanced clarity.

One, or both, of the illuminators 156, 158 may include a multitude of light sources and one or more photo detectors. The light sources may be configured to illuminate at least one portion of a sample positioned on the stage 152 with light at a variety of wavelengths in a sequential order or in a random order. A lens, which may be the lens associated with the eyepiece 144 or one or more of the lenses associated with the objectives 148, may converge incident light from the light sources on and around the portion of the sample to illuminate the portion of the sample. The photo detectors may be positioned within the illuminators 156, 158 such that the light sources surround the photo detectors, where the light sources may be positioned in a circular arrangement, an elliptical arrangement, a rectangular arrangement, or a triangular arrangement. Furthermore, the light sources may be arranged in an array due to their position within the illuminators versus a conventional illumination source, such as the illumination source discussed in conjunction with FIG. 1B. Alternately, the photo detectors may be positioned so as to be physically separate from the light sources. The photo detectors may be configured to detect reflected, transmitted, fluorescent, and/or scattered light from the portion of the sample in response to the illumination through separate red, green, and blue color channels. In some embodiments, the reflected, transmitted, fluorescent, and/or scattered light may be detected at the photo detectors through an additional color channel to provide spectral discrimination.

The microscope 142 may further include an analysis module. The analysis module may be integrated with the microscope 142 and/or may be a part of a computing device coupled to the microscope 142 through wired or wireless communication means. The analysis module of the microscope 142 may be configured to analyze the detected light to determine a spectral profile of the portion of the sample. In some embodiments, the analysis module may be further configured to evaluate the portion of the sample by comparing the spectral profile of the portion of the sample to a spectral profile of a reference sample. The sample may be evaluated to determine an identity, a composition, a quality, an authenticity, a density, a reflectivity, and/or an amount of the sample. For example, a sample of an organic compound may be evaluated to determine a composition, and furthermore a quality of the compound.

Figure 2:
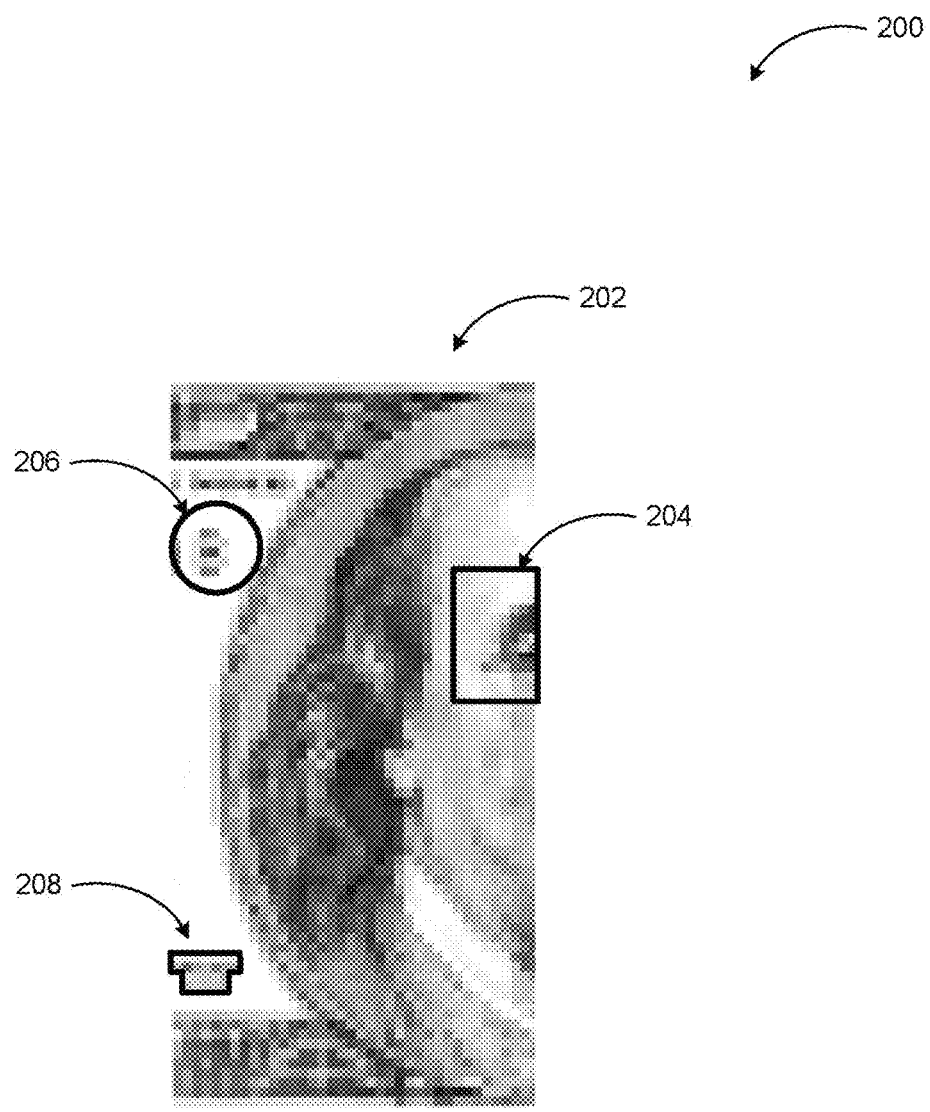
FIG. 2 illustrates an example of returned light from a sample detected in response to illumination of the sample.

FIG. 2 illustrates an example of returned light from a sample detected in response to illumination of the sample, arranged in accordance with at least some embodiments described herein.

A microscope may include one or more optical elements, a multitude of light sources, and one or more photo detectors positioned within the microscope. The microscope may also include an analysis module, where the analysis module may be integrated with the microscope or may be a part of a computing device coupled to the microscope. One or more portions (e.g., 204, 206, and 208) of a sample 202 may be illuminated with light from the light sources. The sample 202 may be a left, center region of a one hundred dollar bill, for example. The first portion 204 may be an area surrounding a left eye of Benjamin Franklin, the second portion 206 may be an area including a part of a serial number associated with the bill, and the third portion 208 may be a region including a design date of the bill. As illustrated by the diagram 200, the photo detectors may detect reflected, transmitted, and/or scattered light from the first portion 204, the second portion 206, and/or the third portion 208. Furthermore, the reflected, transmitted, and/or scattered light may be detected at the photo detectors through separate red, green, and blue color channels. In some embodiments, the reflected, transmitted, and/or scattered light may be detected at the photo detectors through an additional color channel to provide spectral discrimination.

The analysis module may be configured to analyze the detected light from the first portion 204, the second portion 206, and/or the third portion 208 to determine a spectral profile of the one or more portions. For example, the analysis module may record a response from the photo detectors as a function of the light sources selected and the sources' intensity (i.e., a power and/or current supplied to the light sources). The response may be compared to tabulated values in a database. In a comprehensive spectral analysis, the response and comparison process may be repeated for a plurality of illumination sources to build a detailed collection of data comprising multiple wavelengths of light. When at least one of the photo detectors is an imaging device, the analysis may be further directed to correspond to specific portions of the sample within the sampled image. In some embodiments, the first portion 204, the second portion 206, and/or the third portion 208 may be further evaluated based on the spectral profile. For example, a bank teller may be suspicious of fraudulent bills entering the bank, but may not be able to confirm with only a human eye evaluation. Therefore, the first portion 204, the second portion 206, and/or the third portion 208 may be evaluated to determine an authenticity of the sample 202 based on the spectral profile. The first portion 204, the second portion 206, and/or the third portion 208 may be compared to first, second, and/or third portions of a reference sample, where the reference sample may be a one hundred dollar bill known to be authentic, for example.

In some embodiments, the photo detectors may be configured to capture an image in addition to detecting the reflected, transmitted, and/or scattered light. The spectral profile determined from analysis of the detected light and the image data may be linked together automatically for improved analysis. Successful analysis may be indicated to a user of the microscope. Alternately, further data collection may be requested by the user or automatically obtained in response to an unsuccessful analysis.

Figure 3:
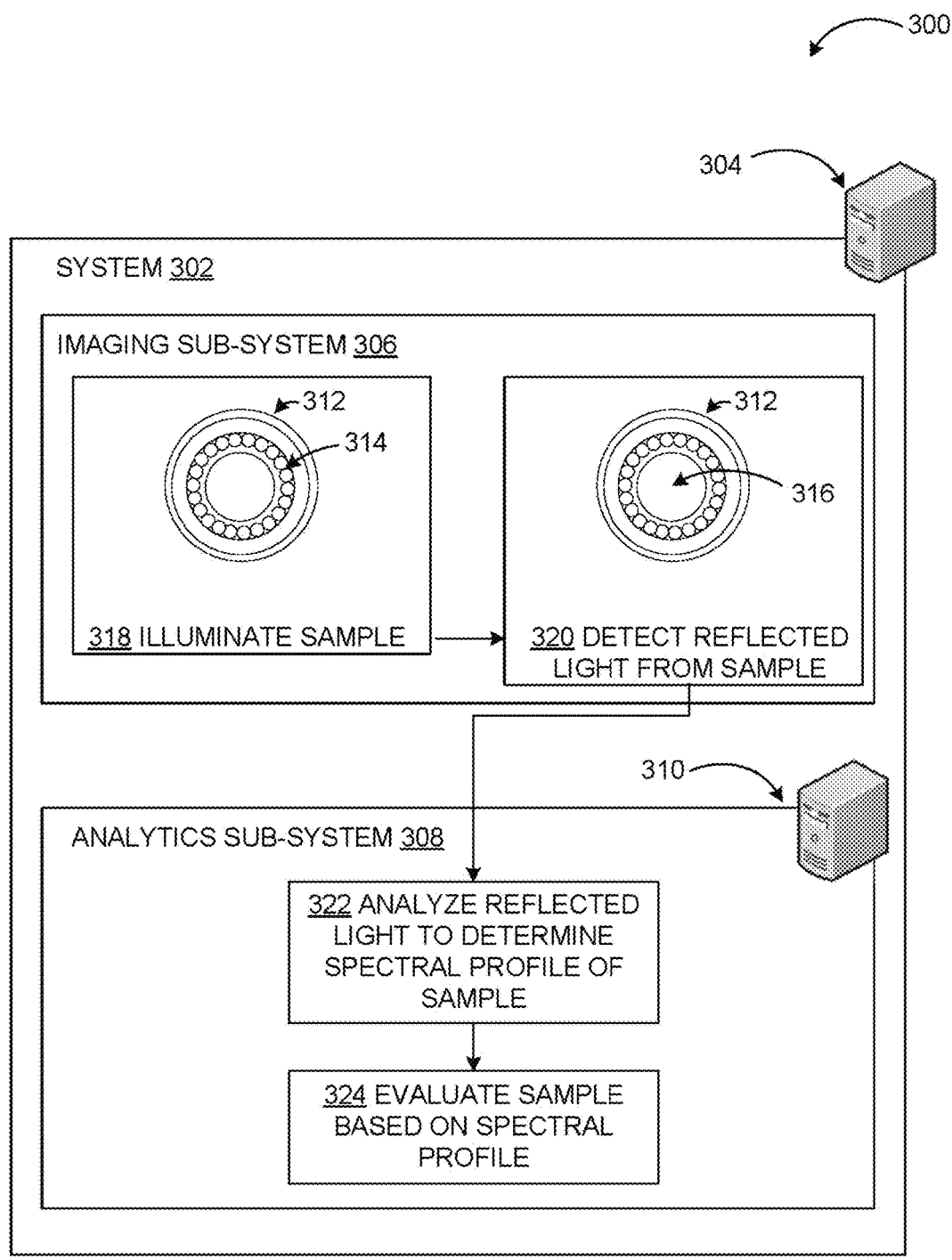
FIG. 3 illustrates an example system configured to determine a spectral profile of a sample.

FIG. 3 illustrates an example system configured to determine a spectral profile of a sample, arranged in accordance with at least some embodiments described herein.

As shown in a diagram 300, an example system 302 configured to determine a spectral profile of a sample may include a controller 304, an imaging sub-system 306, and an analytic sub-system 308. The controller 304 may be configured to control one or more operational aspects of the imaging sub-system 306 and the analytics sub-system 308. The imaging sub-system 306 may include a multitude of light sources 314 and one or more photo detectors 316 positioned within a microscope 312. The light sources 314 may include LEDs, laser diodes, white light sources, UV light sources, infrared light sources, red light sources, orange light sources, yellow light sources, green light sources, blue light sources, and/or violet light sources. The photo detectors 316 may include photodiodes, photomultiplier tubes, CMOS image sensors, CCDs, infrared sensors, thermal sensors, and/or micro-channel plates. The analytics sub-system 308 may include an analysis module of the microscope 312 comprising one or more servers 310.

The imaging sub-system 306 may further include an illumination module and a detection module. The illumination module may be configured to illuminate 318 at least one portion of a sample with light from the light sources 314. The light sources 314 may be selected based on a color and/or identity of the sample. In some embodiments, the portion of the sample may be illuminated with light at a variety of wavelengths in a sequential or random order for a pre-determined period of time. In some examples, the period of time may be custom programmed by a user through one or more tools provided to the user. The detection module may include the photo detectors 316 configured to detect 320 reflected, transmitted, and/or scattered light from the portion of the sample in response to the illumination. The reflected, transmitted, and/or scattered light may be detected at the photo detectors 316 through separate red, green, and blue color channels, and in some embodiments, the reflected, transmitted, and/or scattered light may be detected at the photo detectors 316 through an additional color channel to provide spectral discrimination.

The analytics sub-system 308 may further include a profiling module and an evaluation module executed by the servers 310. The profiling module may be configured to analyze 322 the portion of the sample to determine a spectral profile of the portion of the sample. For example, the analysis module may record a response from the photo detectors 316 as a function of the selected light sources 314 and the sources' intensity (i.e., a power and/or current supplied to the light sources). The response may be compared to tabulated values in a database. In a comprehensive spectral analysis, the response and comparison process may be repeated for a plurality of the light sources 314 to build a detailed collection of data comprising multiple wavelengths of light. When at least one of the photo detectors 316 is an imaging device, the analysis may be further directed to correspond to specific portions of the sample within the sampled image. The evaluation module may be configured to evaluate 324 the portion of the sample based on the spectral profile. For example, the spectral profile of the sample may be compared to a spectral profile of a reference sample such that the sample may be evaluated based on the comparison.

The system 302 may be configured as unitary device, or each sub-system and/or module may be a separate entity. In some examples, the modules may snap and/or connect together to form each sub-system. Furthermore, the modules may be removable and/or interchangeable, so as to customize response to a wide variety of materials.

Figure 4:
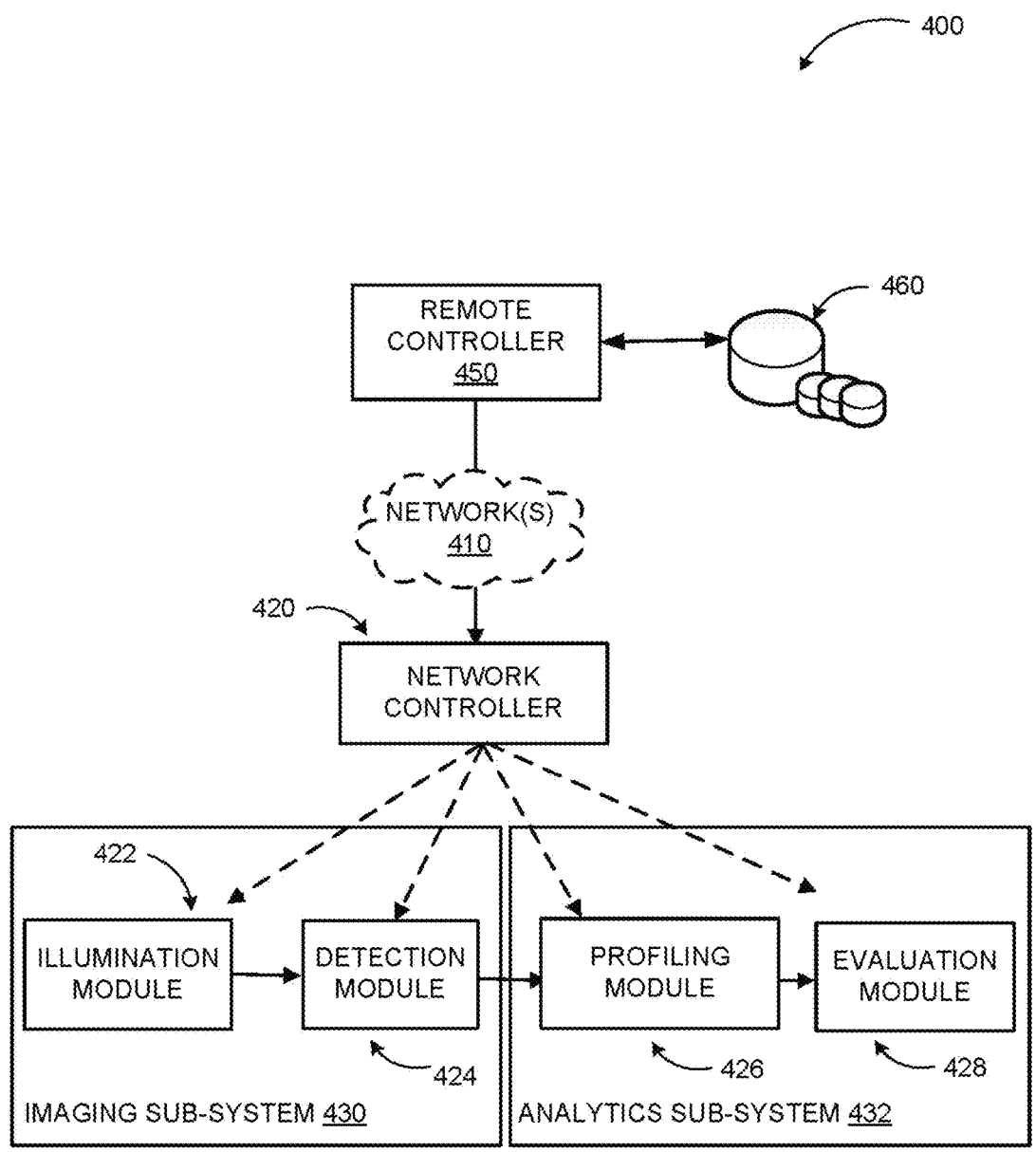
FIG. 4 illustrates an example controller of a system configured to determine a spectral profile of a sample.

FIG. 4 illustrates an example controller of a system configured to determine a spectral profile of a sample, arranged in accordance with at least some embodiments described herein.

System 400 may include at least one controller 420, at least one illumination module 422 and at least one detection module 424 of an imaging sub-system 430, and at least one profiling module 426 and at least one evaluation module 428 of an analytics sub-system 432. The controller 420 may be operated by human control or may be configured for automatic operation, or may be directed by a remote controller 450 through at least one network (for example, via network 410). Data associated with controlling the different processes of production may be stored at or received from data stores 460.

The controller 420 may include or control the illumination module 422 and the detection module 424 of the imaging sub-system 430. The illumination module 422 may be configured to illuminate at least one portion of the sample with light from a multitude of light sources at a variety of wavelengths in a sequential or random order for a predetermined period of time, where the period of time may be custom programmed by a user through one or more tools provided to the user. One or more of the light sources may be operable to emit the light at wavelengths in part or in all of an optical portion of the electromagnetic spectrum, including the visible portion, near-infrared portion and/or near ultraviolet portions of the electromagnetic spectrum. Additionally, or alternatively, the light sources may be operable to emit light at wavelengths in other portions of the electromagnetic spectrum, such as the infrared, ultraviolet, and/or microwave portions. In some embodiments, at least one of the light sources may be operable to emit the light in or at a different wavelength the other light sources, or each of the light sources may emit light at a different wavelength. Due to distribution of spectral content for each of the light sources varying as a function of drive level (for example, current, voltage, and duty cycle), temperature, and/or other environmental factors, depending on a type of the light sources, adjustment of the drive level and/or temperature may cause the peak wavelength to shift, allowing each of the light sources to emit light at a different wavelength such that the portion of the sample may be illuminated with light at a variety of different wavelengths.

In some examples, the sample may be illuminated with the light to initially inspect and determine a target area on the sample for evaluation. In further examples, the illumination module may be configured to illuminate at least a portion of a reference sample to be used for comparison when evaluating the sample. The illumination module 422 may be interchangeable so as to customize response to a wide variety of materials. For example, another set of light sources may be introduced, where the other set of light sources emit light at different wavelengths to enable more comprehensive analysis. The detection module 424 may be configured to detect reflected, transmitted, and/or scattered light from the portion of the sample and/or the portion of the reference sample to be in response to the illumination. The reflected, transmitted, and/or scattered light may be detected at the photo detectors through separate red, green, and blue color channels. In some embodiments, the reflected, transmitted, and/or scattered light may be detected at the photo detectors through an additional color channel to provide spectral discrimination.

The controller 420 may further include or control the profiling module 426 and the evaluation module 428 of the analytics sub-system 432. The profiling module 426 may be configured to determine a spectral profile of the portion of the sample and/or a spectral profile of the portion of the reference sample based on an analysis of the detected light. The evaluation module 428 may be configured to compare the spectral profile of the sample to the spectral profile of a reference sample to evaluate the sample. The sample may be evaluated to determine an identity, a composition, a quality, an authenticity, a density, a reflectivity, and/or an amount of the sample, for example.

In some embodiments, the profiling module 426 and the evaluation module 428 of the analytics sub-system 432 may be a part of a computing device coupled to the microscope through wired or wireless communication means, such as a USB cable, WIFI, Bluetooth, and/or Near-Field Communication (NFC). One or more controls may be incorporated into the microscope causing automatic transmission of image and/or spectral data via the USB cable, WIFI, Bluetooth, and/or Near-Field Communication (NFC) to the computing device for profiling and evaluation. In other embodiments, the profiling module 426 and the evaluation module 428 of the analytics sub-system 432 may be integrated with the microscope causing analyzed image and/or spectral data to be stored in memory local to the microscope for subsequent download and/or comparison with a database.

The examples in FIGS. 1A through 4 have been described using specific apparatuses, configurations, and systems to determine a spectral profile of a sample. Embodiments to determine spectral profiles of samples are not limited to the specific apparatuses, configurations, and systems according to these examples.

Figure 5:
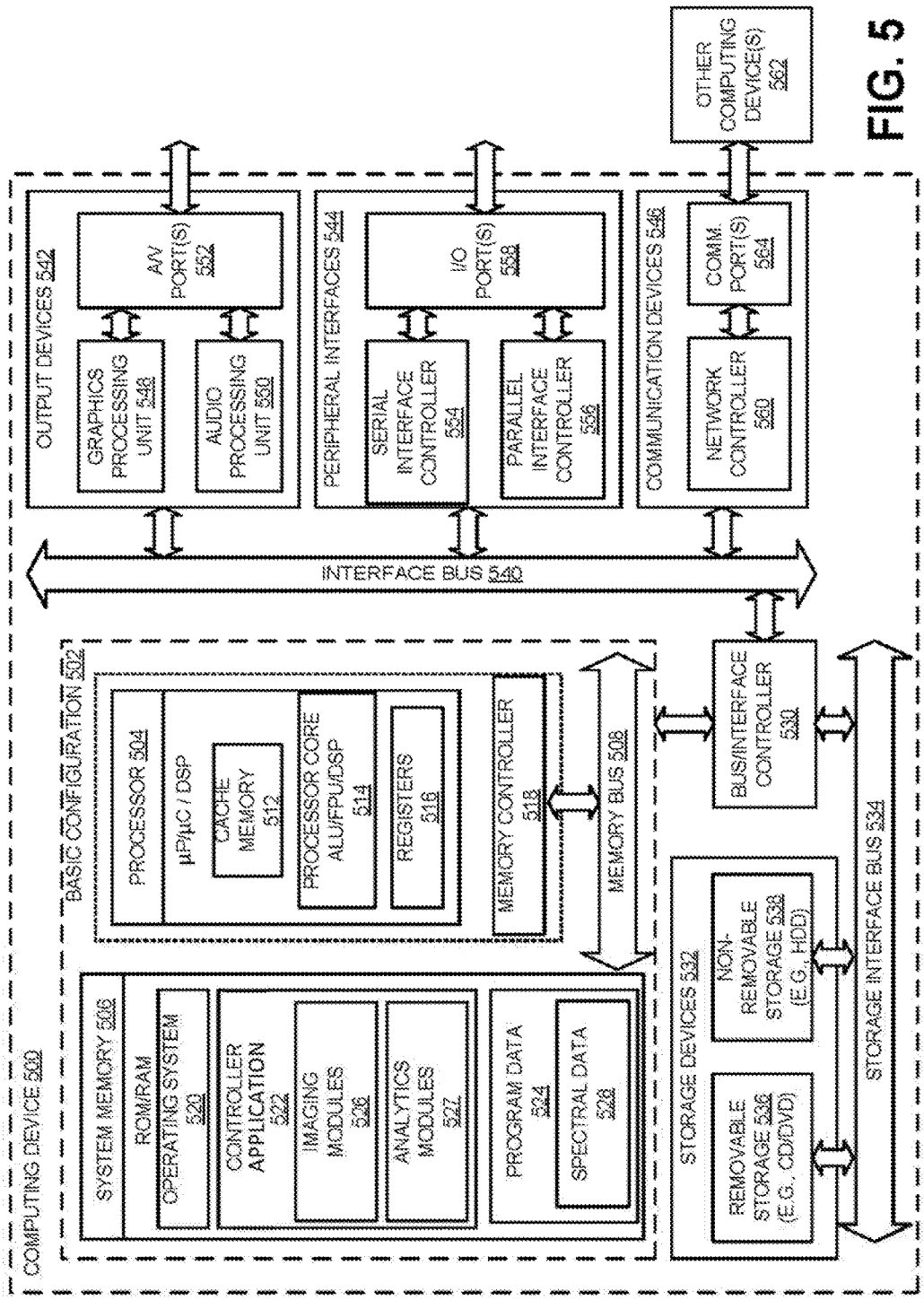
FIG. 5 illustrates a general purpose computing device, which may be used to determine a spectral profile of a sample.

FIG. 5 illustrates a general purpose computing device, which may be used to determine a spectral profile of a sample, arranged in accordance with at least some embodiments described herein.

For example, the computing device 500 may be used as a server, desktop computer, portable computer, smart phone, special purpose computer, or similar device such as a controller, a new component, a cluster of existing components in an operational system including a vehicle and a smart dwelling. In an example basic configuration 502, the computing device 500 may include one or more processors 504 and a system memory 506. A memory bus 508 may be used for communicating between the processor 504 and the system memory 506. The basic configuration 502 is illustrated in FIG. 5 by those components within the inner dashed line.

Depending on the desired configuration, the processor 504 may be of any type, including but not limited to a microprocessor (μP), a microcontroller (μC), a digital signal processor (DSP), or any combination thereof. The processor 504 may include one more levels of caching, such as a cache memory 512, one or more processor cores 514, and registers 516. The example processor cores 514 may (each) include an arithmetic logic unit (ALU), a floating point unit (FPU), a digital signal processing core (DSP Core), or any combination thereof. An example memory controller 518 may also be used with the processor 504, or in some implementations the memory controller 518 may be an internal part of the processor 504.

Depending on the desired configuration, the system memory 506 may be of any type including but not limited to volatile memory (such as RAM), non-volatile memory (such as ROM, flash memory, etc.) or any combination thereof. The system memory 506 may include an operating system 520, a controller application 522, and program data 524. The controller application 522 may include one or more imaging modules 526 and analytics modules 527, which may be an integral part of the application or a separate application on its own. The imaging modules 526 may be configured to illuminate at least one portion of a sample with light from a plurality of light sources positioned in a microscope, and detect reflected, transmitted, and/or scattered light from portion of the sample in response to the illumination at one or more photo detectors positioned in the microscope. The analytics modules 527 may be configured to analyze the detected light to determine a spectral profile for the portion of the sample, and compare the spectral profile of the sample to a spectral profile of a reference sample to evaluate the sample. The program data 524 may include, among other data, spectral data 528 related to the detected light analysis used to determine the spectral profile, as described herein.

The computing device 500 may have additional features or functionality, and additional interfaces to facilitate communications between the basic configuration 502 and any desired devices and interfaces. For example, a bus/interface controller 530 may be used to facilitate communications between the basic configuration 502 and one or more data storage devices 532 via a storage interface bus 534. The data storage devices 532 may be one or more removable storage devices 536, one or more non-removable storage devices 538, or a combination thereof. Examples of the removable storage and the non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

The system memory 506, the removable storage devices 536 and the non-removable storage devices 538 are examples of computer storage media. Computer storage media includes, but is not limited to, RAM, ROM, EEPROM, flash memory or other memory technology, CD-ROM, digital versatile disks (DVDs), solid state drives, or other optical storage, magnetic cassettes, magnetic tape, magnetic disk storage or other magnetic storage devices, or any other medium which may be used to store the desired information and which may be accessed by the computing device 500. Any such computer storage media may be part of the computing device 500.

The computing device 500 may also include an interface bus 540 for facilitating communication from various interface devices (for example, one or more output devices 542, one or more peripheral interfaces 544, and one or more communication devices 546) to the basic configuration 502 via the bus/interface controller 530. Some of the example output devices 542 include a graphics processing unit 548 and an audio processing unit 550, which may be configured to communicate to various external devices such as a display or speakers via one or more A/V ports 552. One or more example peripheral interfaces 544 may include a serial interface controller 554 or a parallel interface controller 556, which may be configured to communicate with external devices such as input devices (for example, keyboard, mouse, pen, voice input device, touch input device, etc.) or other peripheral devices (for example, printer, scanner, etc.) via one or more I/O ports 558. An example communication device 546 includes a network controller 560, which may be arranged to facilitate communications with one or more other computing devices 562 over a network communication link via one or more communication ports 564. The one or more other computing devices 562 may include servers, client devices, and comparable devices.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 500 may be implemented as a part of a general purpose or specialized server, mainframe, or similar computer that includes any of the above functions. The computing device 500 may also be implemented as a personal computer including both laptop computer and non-laptop computer configurations.

Example embodiments may also include methods to determine a spectral profile of a sample. These methods can be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. These human operators need not be collocated with each other, but each can be only with a machine that performs a portion of the program. In other embodiments, the human interaction can be automated such as by pre-selected criteria that may be machine automated.

Figure 6:
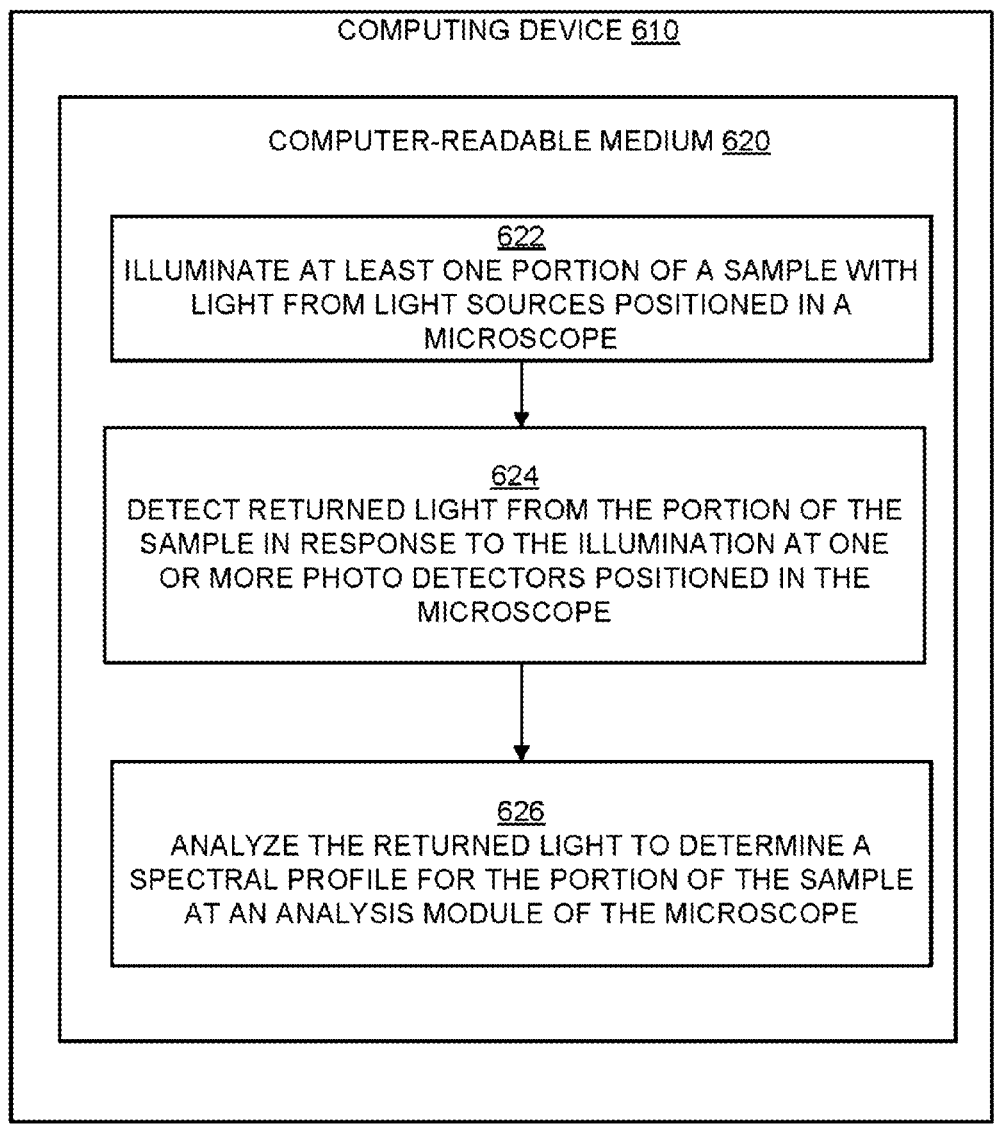
FIG. 6 is a flow diagram illustrating an example process to determine a spectral profile of a sample that may be performed by a computing device such as the computing device in FIG. 5.

FIG. 6 is a flow diagram illustrating an example process to determine a spectral profile of a sample that may be performed by a computing device such as the computing device in FIG. 5, arranged in accordance with at least some embodiments described herein.

Example methods may include one or more operations, functions or actions as illustrated by one or more of blocks 622, 624, and/or 626. The operations described in the blocks 622 through 626 may also be stored as computer-executable instructions in a computer-readable medium such as a computer-readable medium 620 of a computing device 610.

An example process to determine a spectral profile of a sample may begin with block 622, "ILLUMINATE AT LEAST ONE PORTION OF A SAMPLE WITH LIGHT FROM LIGHT SOURCES POSITIONED IN A MICROSCOPE," where at least one portion of a sample may be illuminated with light from a multitude of lights sources at a variety of wavelengths in a sequential or random order for a pre-determined time period. The light sources may be positioned within a microscope, where the microscope may be a hand-held microscope or a table-top microscope. The light sources may be positioned in circular arrangement, an elliptical arrangement, a rectangular arrangement, or a triangular arrangement. In some examples, where the microscope is a table-top microscope comprising one or more episcopic and/or diascopic illuminators, the light sources may be further positioned in an array. The light sources may include LEDs, laser diodes, white light sources, UV light sources, infrared light sources, red light sources, orange light sources, yellow light sources, green light sources, blue light sources, and/or violet light sources, for example. The type of light sources selected may be dependent on a color and/or an identity of the sample. In some embodiments, indicator light source, such as light from the white LEDs may be used to illuminate the sample to initially inspect and determine a target area on the sample for evaluation.

Block 622 may be followed by block 624, "DETECT RETURNED LIGHT FROM THE PORTION OF THE SAMPLE IN RESPONSE TO THE ILLUMINATION AT ONE OR MORE PHOTO DETECTORS POSITIONED IN THE MICROSCOPE," where one or more photo detectors positioned in the microscope may be configured to detect returned light from the sample. In some examples, transmitted and/or scattered light from the sample may also be detected by the photo detectors. The returned light may be detected at the photo detectors through separate red, green, and blue color channels, and in some embodiments, the returned light may be detected at the photo detectors through an additional color channel to provide spectral discrimination. The photo detectors may include photodiodes, photomultiplier tubes, CMOS image sensors, CCDs, infrared sensors, thermal sensors, and/or micro-channel plates. In some examples, the photo detectors may be positioned in the microscope such that the light sources surround the photo detectors. The microscope may also include at least one light blocking filter configured to reduce a portion of light from the light sources directed to the photo detectors when illuminating the sample.

Block 624 may be followed by block 626, "ANALYZE THE DETECTED LIGHT TO DETERMINE A SPECTRAL PROFILE FOR THE PORTION OF THE SAMPLE AT AN ANALYSIS MODULE OF THE MICROSCOPE," where an analysis module of the microscope may be configured to determine a spectral profile of the sample based on an analysis of the detected light. The analysis module may integrated with the microscope and/or may be a part of a computing device coupled to the microscope through wired or wireless communication means, such as a USB cable, WIFI, Bluetooth, and/or Near-Field Communication (NFC). In some examples, the spectral profile of the sample may be compared to a spectral profile of a reference sample to evaluate the sample, where the sample may be evaluated to determine an identity, a composition, a quality, an authenticity, a density, a reflectivity, and/or an amount of the sample.

In some embodiments, the photo detectors may be configured to capture an image in addition to detecting the reflected, transmitted, and/or scattered light. The spectral profile determined from analysis of the detected light and the image data may be linked together automatically for improved analysis. Successful analysis may be indicated to a user of the microscope. Alternately, further data collection may be requested by the user or automatically obtained in response to an unsuccessful analysis.

The blocks included in the above described process are for illustration purposes. Determination of a spectral profile of a sample may be implemented by similar processes with fewer or additional blocks. In some embodiments, the blocks may be performed in a different order. In some other embodiments, various blocks may be eliminated. In still other embodiments, various blocks may be divided into additional blocks, or combined together into fewer blocks.

Figure 7:
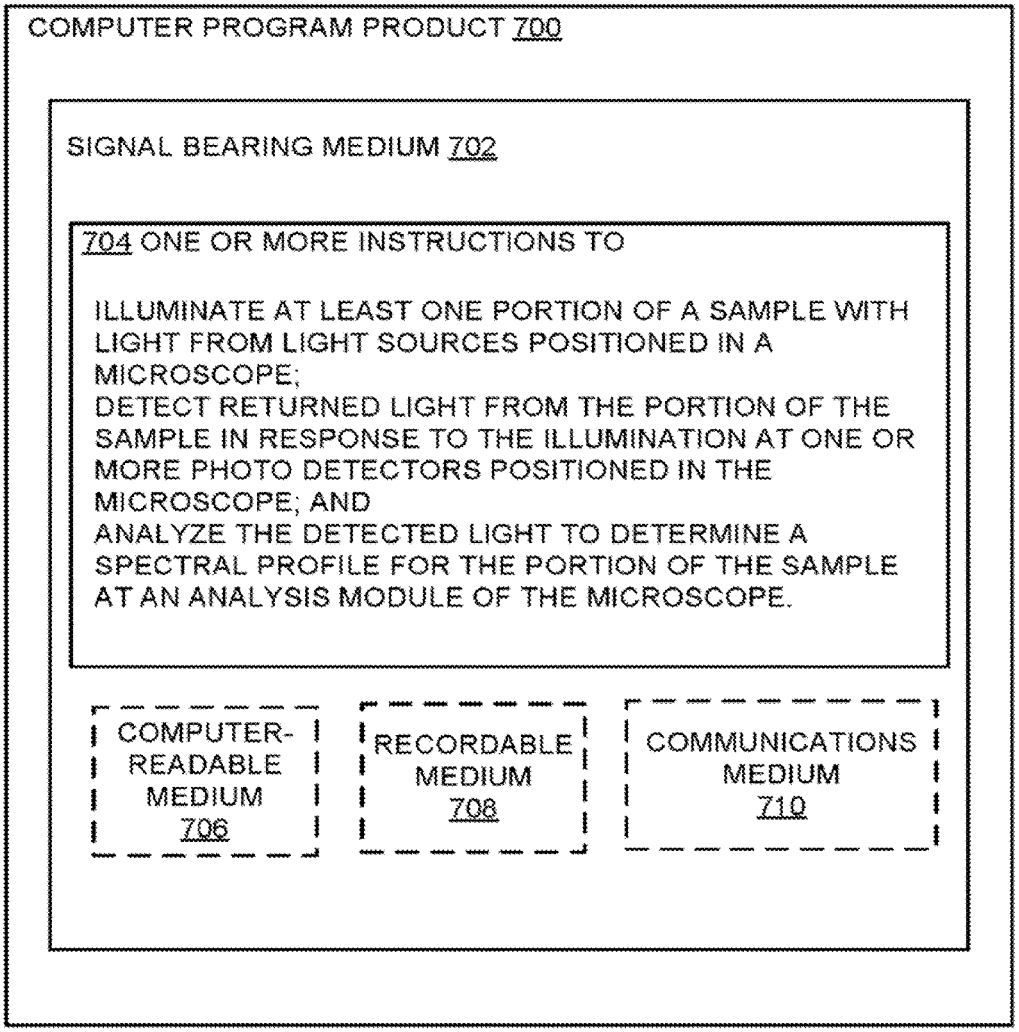
FIG. 7 illustrates a block diagram of an example computer program product, all arranged in accordance with at least some embodiments described herein.

FIG. 7 illustrates a block diagram of an example computer program product, arranged in accordance with at least some embodiments described herein.

In some embodiments, as shown in FIG. 7, the computer program product 700 may include a signal bearing medium 702 that may also include one or more machine readable instructions 704 that, when executed by, for example, a processor, may provide the functionality described herein. Thus, for example, referring to the processor 504 in FIG. 5, imaging modules 526 and analytics modules 527 executed on the processor 504 may undertake one or more of the tasks shown in FIG. 7 in response to the instructions 704 conveyed to the processor 504 by the signal bearing medium 702 to perform actions associated with determination of a spectral profile of a sample as described herein. Some of those instructions may include, for example, one or more instructions to illuminate at least one portion of a sample with light from light sources positioned in a microscope, detect returned light from the portion of the sample in response to the illumination at one or more photo detectors positioned in the microscope, and analyze the detected light to determine a spectral profile for the portion of the sample at an analysis module of the microscope.

In some implementations, the signal bearing medium 702 depicted in FIG. 7 may encompass a computer-readable medium 706, such as, but not limited to, a hard disk drive (HDD), a solid state drive (SSD), a Compact Disc (CD), a Digital Versatile Disk (DVD), a digital tape, memory, etc. In some implementations, the signal bearing medium 702 may encompass a recordable medium 708, such as, but not limited to, memory, read/write (R/W) CDs, R/W DVDs, etc. In some implementations, the signal bearing medium 702 may encompass a communications medium 710, such as, but not limited to, a digital and/or an analog communication medium (for example, a fiber optic cable, a waveguide, a wired communications link, a wireless communication link, etc.). Thus, for example, the computer program product 700 may be conveyed to one or more modules of the processor 504 of FIG. 5 by an RF signal bearing medium, where the signal bearing medium 702 is conveyed by the wireless communications medium 710 (for example, a wireless communications medium conforming with the IEEE 802.11 standard).

According to some examples, microscopes with spectroscopic capability may be described. An example microscope may include a plurality of light sources positioned within the microscope, where the light sources may be configured to illuminate at least one portion of a sample; and one or more photo detectors positioned within the microscope such that the light sources surround the photo detectors, where the photo detectors may be configured to detect returned light from the portion of the sample in response to the illumination. The example microscope may also include an analysis module configured to analyze the detected light to determine a spectral profile of the portion of the sample.

In other examples, the light sources may include light emitting diodes (LEDs), laser diodes, and white light sources, ultraviolet (UV) light sources, infrared light sources, red light sources, orange light sources, yellow light sources, green light sources, blue light sources, and/or violet light sources. The photo detectors may include photodiodes, photomultiplier tubes, complementary metal oxide semiconductor (CMOS) image sensors, charged coupled devices (CCDs), infrared sensors, thermal sensors, and/or microchannel plates. One or more polarizer elements may be integrated with the light sources and the photo detectors to provide a polarized light microscope, where the polarized light microscope may be configured to provide a glare control, a discrimination of roughness variations, and/or a relative stress indication.

In further examples, the microscope may also include at least one light blocking filter configured to reduce a portion of light from the light sources directed to the photo detectors when illuminating the at least one portion of the sample. The microscope may further include one or more optical elements, wherein the optical elements include one or more lenses, reflectors, and partial reflectors. The microscope may yet further include a lens configured to converge incident light from the light sources on to the portion of the sample to illuminate the portion of the sample. The light sources may be arranged in one of a circular arrangement, an elliptical arrangement, a rectangular arrangement, or a triangular arrangement. Analysis data may be stored in memory local to the microscope for subsequent download and comparison with a database. The analysis module may be coupled to a computing device through wired or wireless communication means, where the computing device may be configured to analyze the detected light to determine the spectral profile of the portion of the sample, and store analysis data in memory local to the computing device.

According to some embodiments, systems to determine a spectral profile of a sample are described. An example system may include an imaging sub-system and an analytics sub-system. The imaging sub-system may include an illumination module configured to illuminate at least one portion of the sample with light from a plurality of light sources positioned within a microscope; and a detection module configured to detect returned light from the portion of the sample in response to the illumination at one or more photo detectors positioned within the microscope. The analytics sub-system may include one or more servers coupled to the imaging sub-system, the one or more servers configured to execute a profiling module configured to analyze the detected light to determine a spectral profile of the portion of the sample; and an evaluation module configured to evaluate one or more characteristics of the at least one portion of the sample based on the determined spectral profile.

In other embodiments, the microscope may be a hand-held microscope or a table-top microscope. The illumination module, detection module, profiling module, and/or evaluation module may be separate, interchangeable modules of the system. The illumination module, detection module, profiling module, and evaluation module may be a single unit integrated within the microscope. The system may also include at least one controller configured to control one or more operational aspects of the imaging sub-system and the analytics sub-system. The illumination module may be configured to illuminate the at least one portion of the sample with the light from the plurality of light sources at a variety of wavelengths in one of a sequential order or a random order for a pre-determined time period.

According to some examples, methods to determine a spectral profile of a sample are provided. An example method may include sequentially illuminating at least one portion of the sample at a variety of wavelengths from a plurality of light sources positioned in a microscope, detecting returned light from the portion of the sample in response to the illumination at one or more photo detectors positioned in the microscope, and analyzing the returned light to determine the spectral profile of the portion of the sample.

In other examples, the spectral profile of the portion of the sample may be compared to a spectral profile of at least one portion of a reference sample to evaluate the portion of the sample based on the comparison. The portion of the reference sample may be retrieved from a memory local to the microscope or downloaded from a database configured to store spectral analysis data. The portion of the sample may be evaluated to an identity, a composition, a quality, an authenticity, a density, a reflectivity, and/or an amount of the portion of the sample.

In further examples, the returned light may be detected at the photo detectors through separate red, green, and blue color channels, where the returned light may be detected at the photo detectors through an additional color channel to provide spectral discrimination. A voltage or a current supplied to one or more of the light sources may be adjusted to cause a peak wavelength of the one or more of the light sources to shift. The shift in the peak wavelength of the one or more of the light sources may allow the one or more of the light sources to emit light at a different wavelength such that the portion of the sample may be sequentially illuminated with light at the variety of wavelengths.

EXAMPLES

Following are illustrative examples of how some embodiments may be implemented, and are not intended to limit the scope of embodiments in any way.

Example 1

Transportation Security Evaluating an Authenticity of a Passport Using a Hand-Held, Polarized Light Microscope In most domestic and international airports, transportation security requires passengers to present identification along with their airline ticket. Many forms of government issued identification documents include authenticity features such as UV-visible text or graphics, very small text or graphics, holograms, and similar ones. Security personnel may evaluate the authenticity of an identification document using a hand-held microscope. The microscope includes one or more optical elements, such as a lens, a multitude of light sources, and one or more photo detectors positioned within the microscope. One or more polarizer elements are integrated with the light sources and the photo detectors, which provide a glare control, a discrimination of roughness variations, and a relative stress indication. The microscope also includes an analysis module, integrated with the microscope.

The light sources are light emitting diodes (LEDs) positioned in a circular arrangement within the microscope. Initially, white LEDs are used to illuminate the identification document to inspect and determine a target area on the identification document for evaluation. The target area is a holographic portion of the identification document. The LEDs are configured to illuminate the holographic portion with light, where the lens converges incident light from the LEDs on and around the holographic portion of the identification document to illuminate. The holographic portion of the identification document is then illuminated with the light at a variety of wavelengths in a sequential order. The photo detectors are CMOS image sensors positioned within the microscope such that the LEDs surround the CMOS image sensors, where the CMOS image sensors are configured to detect returned light from the holographic portion of the identification document in response to the illumination. Additionally, the CMOS image sensors are configured to capture an image in addition to detecting the returned light.

The analysis module is configured to analyze the returned light to determine a spectral profile of the holographic portion of the identification document and evaluate the holographic portion of the identification document based on the spectral profile to determine the authenticity. The spectral profile determined from analysis of the returned light and the image data are linked together automatically for improved analysis. Successful analysis is indicated to transportation security. Alternately, further data collection may be requested by transportation security or automatically obtained in response to an unsuccessful analysis.

Example 2

Law Enforcement Evaluating a Liquid to Identify the Liquid Using a Hand-Held Microscope A law enforcement officer at a college campus suspects a student of possessing an illicit drug after viewing the student place a small bag containing a white, chalky powder into a backpack. The identity of the powder is determined using a hand-held microscope. The microscope includes one or more optical elements, such as a lens, a multitude of light sources, and one or more photo detectors positioned within the microscope. The microscope also includes an analysis module, which is integrated with the microscope.

The light sources are laser diodes positioned in a rectangular arrangement within the microscope. The laser diodes are configured to illuminate at least a portion of the powder, such as a top surface of the liquid, with light, where the lens converges incident light from the laser diodes on to powder to illuminate. The powder is illuminated with the light at a variety of wavelengths in a random order. The microscope includes at least one light blocking filter to reduce a portion of light from the laser diodes directed to the photo detectors when illuminating the powder.

The photo detectors are charged coupled devices (CCDs) positioned within the microscope such that the laser diodes surround the CCDs, where the CCDs are configured to detect reflected, transmitted, and scattered light from the powder in response to the illumination. The analysis module is configured to analyze the returned light to determine a spectral profile of the powder and evaluate the powder based on the spectral profile to determine an identity of the powder. The powder is evaluated by comparing the spectral profile of the powder to one or more spectral profiles of known illicit drugs.

Upon determining the powder to include a high concentration of a known illicit drug, the law enforcement officer places the student under arrest.

Example 3

Industrial Chemist Evaluating Fuel to Determine Presence of Contaminants Using a Table-Top Microscope To ensure quality control, an industrial chemist is required to determine if contaminants are present in fuel, where the fuel is stored in tanks. The chemist evaluates the quality of the fuel using a table-top microscope. The microscope includes a body tube comprising at least one lens, one or more objectives each comprising a lens, and an illumination source providing white light for visual inspection of samples. The microscope further includes a multitude of light sources and one or more photo detectors. The light sources and photo detectors are positioned internally within a body tube of the microscope. The microscope also includes an analysis module, which is a part of a computing device coupled with the microscope through a universal serial bus (USB) connection.

The light sources are infrared (IR) light sources positioned in an elliptical arrangement within the microscope. The IR light sources are configured to illuminate a portion of the fuel with light. The portion of fuel evaluated with the microscope is collected from a bottom surface of the tank, where contaminants are most likely to settle, and placed in a petri dish for evaluation. The lens of the body tube and one or more of the lenses of the objectives converge incident light from the IR light sources on and around the portion of fuel to illuminate.

The photo detectors are photodiodes positioned within the microscope such that the UV light sources surround the photodiodes, where the photodiodes are configured to detect returned light from the portion of fuel in response to the illumination. The analysis module is configured to analyze the returned light to determine a spectral profile of the portion of fuel and evaluate the portion of fuel based on the spectral profile to determine a quality of the fuel. The portion of the fuel is evaluated by comparing the spectral profile of the portion of the fuel to one or more spectral profiles of known fuels that do not contain contaminants.

There are various vehicles by which processes and/or systems and/or other technologies described herein may be effected (for example, hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

In some examples, a microscope with spectroscopic capability comprises a plurality of light sources positioned within the microscope, the plurality of light sources configured to illuminate at least one portion of a sample, and one or more photo detectors positioned within the microscope. In some examples, the plurality of light sources surrounds the one or more photo detectors. In some examples, the one or more photo detectors are configured to detect reflected or otherwise returned light from the at least one portion of the sample in response to the illumination. An example microscope may include an analysis module configured to analyze the detected light to determine a spectral profile of the at least one portion of the sample. For example, photo detector signals from one or more photo detectors may be analyzed as a function of the corresponding illuminated light source. For example, a spectral reflectance may be determined by sequentially illuminating a plurality of light sources having different emission wavelengths. The light sources may, for example, comprise light emitting diodes (LEDs), laser diodes, other light sources, or a combination thereof. In some examples, a fluorescence signal may be analyzed, for example by illuminating a light source (such as a blue, violet, or UV LED) as an excitation light source for the fluorescence emission.

In some examples, the at least one portion of the sample may be selected or adjusted using one or more optical elements. In some examples, one or more optical elements, such as a converging lens, may be used to focus illuminating radiation from a light source on and around the at least one portion of the sample. In some examples, one or more optical elements may be used as magnifying optics for the one or more photo detectors. The photo detectors and magnifying optics may be configured so that the photo detector is selectively responsive to light returned from a spatially defined region of the sample, which may have a cross-sectional diameter in the range from about 1 micron to about 5 mm, for example. In some examples, a laser diode or other light source may be used to visually indicate the spatially defined region of the sample to a user. For example, an indicator light source may be used to illuminate the at least one portion of the sample, allowing a user to select a portion of interest. The user may then press a button or otherwise initiate collection of spectral data from the illuminated portion of the sample. The indicator light source may be turned off during illumination of the sample during spectral data collection, or used as one of the light sources for spectral data collection.

In some examples, the magnification of the magnifying optics may be adjusted by adjusting relative separations of optical elements (such as lenses) and the sample, for example by adjusting a lens-lens separation and/or lens sample separation. In some examples, the magnification of the magnifying optics may be adjusted by selecting one or more optical elements from a plurality of optical elements. For example, a plurality of converging lenses of different focal lengths may be supported by a lens support, and the lens support rotated and/or translated to select a converging lens. The magnifying optics may have a magnification selectable or adjustable between magnifications of 5×, 10×, 20×, 50×, 100×, and the like. The magnification selected may be a function of a degree of detail needed and a size of a sample being characterized and/or evaluated. In some examples, an image sensor of the microscope may be used to obtain an image of the portion of the sample, which may be stored in memory and associated with spectral data obtained from that portion of the sample.

In some examples, a microscope with spectroscopic capability may be used in conjunction with one or more other portable electronic devices, such as a smart phone or head-mounted display. In some examples, an image of the portion of the sample of interest may be transmitted to a portable electronic device such as a smart phone and displayed on the display thereof. The spatial location and extent of the portion may be adjusted using, for example, magnifying optics within the microscope. In some examples, an application on the portable electronic device may be used to control the microscope. For example, once a desired portion of the sample is selected, a displayed button icon on the screen of the portable electronic device may be touched, initiating collection of spectral data. The spectral data may be displayed and/or stored in memory (e.g. of the portable electronic device) together with the image of the portion of the sample from which it was collected. In some examples, a user may view an image of the sample and associate spectral data using a head-mounted display.

In some examples, an analysis module may be used to identify a sample from the collected spectral data. In some examples, a category of object and/or physical description thereof may be input by a user. For example, a user may enter "white powder" into the microscope (using buttons, selectable menu items, voice recognition, or other suitable user input mechanism), or using a portable electronic device in communication with the microscope. The analysis module may then compare collected spectral data with a restricted selection of reference spectral data, based on the selected category. For example, the category of "white powder" may select reference spectral data relating to toiletries, illegal drugs, selected foods, chemicals, and the like. The microscope (or portable electronic device in communication with the microscope) may then indicate a match to the user, for example by audibly annunciating or displaying a message such as "The white powder is an illegal drug. You are under arrest." In some examples, the analysis module may be provided by a portable electronic device in communication with the microscope. In some examples, the microscope may be a component of a robotic peace officer.

In some examples, an optical element may be translated or rotated to scan the location of the portion of interest over a surface of the sample. For example, spectral data may be obtained from a portions of interest obtained in a raster scan. In some examples, the scan speed may be inversely correlated with magnification, for example obtaining more spectral data samples from the sample using a higher magnification, and a correspondingly longer scan time.

While various compositions, methods, systems, and devices are described in terms of "comprising" various components or steps (interpreted as meaning "including, but not limited to"), the compositions, methods, systems, and devices can also "consist essentially of" or "consist of" the various components and steps, and such terminology should be interpreted as defining essentially closed-member groups.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, may be equivalently implemented in integrated circuits, as one or more computer programs running on one or more computers (for example, as one or more programs running on one or more computer systems), as one or more programs running on one or more processors (for example as one or more programs running on one or more microprocessors), as firmware, or as virtually any combination thereof, and that designing the circuitry and/or writing the code for the software and/or firmware would be possible in light of this disclosure.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, will be possible from the foregoing descriptions. Such modifications and variations are intended to fall within the scope of the appended claims. The present disclosure includes the terms of the appended claims, along with the full scope of equivalents to which such claims are entitled. It is to be understood that this disclosure is not limited to particular methods, systems, or components, which can, of course, vary. It is also to be understood that the terminology used herein is for the purpose of describing particular embodiments only, and is not intended to be limiting.

In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (for example, a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that particular functionality is achieved. Hence, any two components herein combined to achieve a particular functionality may be seen as "associated with" each other such that the particular functionality is achieved, irrespective of architectures or intermediate components. Likewise, any two components so associated may also be viewed as being "operably connected", or "operably coupled", to each other to achieve the particular functionality, and any two components capable of being so associated may also be viewed as being "operably couplable", to each other to achieve the particular functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

For any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments are possible. The various aspects and embodiments disclosed herein are for purposes of illustration and are not intended to be limiting, with the true scope and spirit being indicated by the following claims.

What is claimed is:

1. A microscope with spectroscopic capability, the microscope comprising:
a plurality of light sources positioned within the microscope, the plurality of light sources configured to illuminate at least one portion of a sample at a plurality of wavelengths in one of a sequential order or a random order for a pre-determined time period;
one or more photo detectors positioned within the microscope such that the plurality of light sources surround the one or more photo detectors, the one or more photo detectors configured to detect returned light from the at least one portion of the sample in response to the illumination;
one or more input elements positioned on the microscope, wherein a category or a physical description of the sample is entered through the one or more input elements; and
an analysis module configured to:
analyze the detected light to determine a spectral profile of the at least one portion of the sample; and
compare the spectral profile of the at least one portion of the sample with a restricted selection of spectral profiles of reference samples based on the category or the physical description of the sample entered through the one or more input elements.

2. The microscope of claim 1, wherein the plurality of light sources comprise one of light emitting diodes (LEDs) and laser diodes, and one or more of white light sources, ultraviolet (UV) light sources, infrared light sources, red light sources, orange light sources, yellow light sources, green light sources, blue light sources, or violet light sources.

3. The microscope of claim 1, wherein the one or more photo detectors include one or more of photodiodes, photomultiplier tubes, complementary metal oxide semiconductor (CMOS) image sensors, charged coupled devices (CCDs), infrared sensors, thermal sensors, and micro-channel plates.

4. The microscope of claim 1, further comprising:
one or more polarizer elements integrated with the plurality of light sources and the one or more photo detectors, to provide a polarized light microscope configured to provide one or more of a glare control, a discrimination of roughness variations, and a relative stress indication.

5. The microscope of claim 1, further comprising:
at least one light blocking filter configured to reduce a portion of light from the plurality of light sources directed to the one or more photo detectors when illuminating the at least one portion of the sample.

6. The microscope of claim 1, further comprising:
one or more optical elements including one or more lenses, reflectors, and partial reflectors, wherein at least one lens of the one or more lenses is configured to converge incident light from the plurality of light sources on to the at least one portion of the sample to illuminate the at least one portion of the sample.

7. The microscope of claim 1, wherein analysis data is stored in a memory local to the microscope for subsequent download and comparison with a database.

8. The microscope of claim 1, wherein the analysis module is coupled to a computing device through wired or wireless communication means, the computing device configured to analyze the detected light to determine the spectral profile of the at least one portion of the sample, and store analysis data in a memory local to the computing device.

9. A system to determine a spectral profile of a sample, the system comprising:
an imaging sub-system comprising:
an illumination module configured to:
illuminate the sample to determine a target area of the sample for evaluation with an indicator light source, wherein the indicator light source is a light source from a plurality of light sources positioned in a microscope; and
illuminate the target area of the sample with light from the plurality of light sources positioned within the microscope at a plurality of wavelengths in one of a sequential order or a random order for a particular time period; and
a detection module configured to detect returned light from the target area of the sample, in response to the illumination, at one or more photo detectors positioned within the microscope; and
an analytics sub-system comprising one or more servers coupled to the imaging sub-system, the one or more servers configured to execute:
a profiling module configured to analyze the detected light to determine a spectral profile of the target area of the sample; and
an evaluation module configured to evaluate one or more characteristics of the target area of the sample based on the determined spectral profile.

10. The system of claim 9, wherein the microscope is a hand-held microscope or table-top microscope.

11. The system of claim 9, wherein one or more of the illumination module, detection module, profiling module, and evaluation module are separate, interchangeable modules of the system.

12. The system of claim 9, wherein the illumination module, detection module, profiling module, and evaluation module are area single unit integrated within the microscope.

13. The system of claim 9, further comprising:
at least one controller configured to control one or more operational aspects of the imaging sub-system and the analytics sub-system.

14. The system of claim 9, wherein the illumination module is configured to sequentially illuminate the target area of the sample with each light source of the plurality of light sources, and wherein each light source has a different emission wavelength.

15. A method to determine a spectral profile of a sample, the method comprising:
illuminating the sample to determine a target area of the sample for evaluation with an indicator light source, wherein the indicator light source is a light source from plurality of light sources positioned in a microscope;
illuminating the target area of the sample at a plurality of wavelengths in one of a sequential order or a random order for a particular time period from the plurality of light sources positioned in the microscope;
detecting returned light from the target area of the sample, in response to the illumination, at one or more photo detectors positioned in the microscope;
analyzing the returned light to determine a spectral profile of the target area of the sample; and
comparing the spectral profile of the target area of the sample with a restricted selection of spectral profiles of reference samples based on a category or a physical description of the sample, entered through one or more input elements positioned on the microscope, to evaluate the target area of the sample based on the comparison.

16. The method of claim 15 wherein the target area of the sample is evaluated to determine one or more of an identity, a composition, a quality, an authenticity, a density, a reflectivity, and an amount of the target area of the sample.

17. The method of claim 16, wherein the spectral profiles of the reference samples are one of retrieved from a memory local to the microscope or downloaded from a database configured to store spectral analysis data.

18. The method of claim 15, further comprising
detecting the returned light at the one or more photo detectors through separate red, green, and blue color channels.

19. The method of claim 18, wherein the returned light is detected at the one or more photo detectors through an additional color channel to provide spectral discrimination.

20. The method of claim 15, further comprising:
adjusting a voltage or a current supplied to one or more of the plurality of light sources to cause a peak wavelength of the one or more of the plurality of light sources to shift, wherein the shift in the peak wavelength of the one or more of the plurality of light sources allows the one or more of the plurality of light sources to emit light at a different wavelength such that the target area of the sample is sequentially illuminated with light at the plurality of wavelengths.

* * * * *

UNITED STATES PATENT AND TRADEMARK OFFICE
CERTIFICATE OF CORRECTION

PATENT NO. : 9,625,370 B2  
APPLICATION NO. : 14/417135  
DATED : April 18, 2017  
INVENTOR(S) : Bawolek Page 1 of 1

It is certified that error appears in the above-identified patent and that said Letters Patent is hereby corrected as shown below:

In the Specification

In Column 1, Line 8, delete "§371" and insert -- § 371 --, therefor.

In the Claims

In Column 26, Line 32, in Claim 10, delete "or table-top" and insert -- or a table-top --, therefor.

In Column 26, Line 39, in Claim 12, delete "are area" and insert -- are a --, therefor.

In Column 26, Line 54, in Claim 15, delete "from" and insert -- from a --, therefor.

Signed and Sealed this  
Eighth Day of August, 2017

Joseph Matal  
*Performing the Functions and Duties of the*  
*Under Secretary of Commerce for Intellectual Property and*  
*Director of the United States Patent and Trademark Office*